United States Patent [19]

Snipes

[11] Patent Number: 5,244,668
[45] Date of Patent: Sep. 14, 1993

[54] LOW-MELTING MOLDABLE PHARMACEUTICAL EXCIPIENT AND DOSAGE FORMS PREPARED THEREWITH

[75] Inventor: Wallace C. Snipes, Pine Grove Mills, Pa.

[73] Assignee: Zetachron, Inc., State College, Pa.

[21] Appl. No.: 930,325

[22] Filed: Aug. 17, 1992

Related U.S. Application Data

[60] Division of Ser. No. 677,573, Mar. 29, 1991, Pat. No. 5,139,790, which is a division of Ser. No. 264,747, Oct. 31, 1988, Pat. No. 5,004,601, which is a continuation-in-part of Ser. No. 257,569, Oct. 14, 1988, Pat. No. 5,135,752.

[51] Int. Cl.$^5$ .......................... A61K 9/02; A61K 9/06; A61K 9/20; A61K 31/74
[52] U.S. Cl. ..................................... 424/435; 424/436; 424/452; 424/465; 424/486; 424/501; 514/770; 514/784; 514/813; 514/874; 514/960; 514/966; 514/967; 514/969; 514/953
[58] Field of Search ............... 424/435, 436, 452, 465, 424/486, 501; 514/770, 960, 967, 966, 953

[56] References Cited

U.S. PATENT DOCUMENTS

| | | | |
|---|---|---|---|
| 3,873,485 | 3/1975 | Fichera | 524/612 |
| 4,911,859 | 3/1990 | Bunczk et al. | 252/106 |
| 5,004,601 | 4/1991 | Snipes | 514/772.7 |
| 5,019,311 | 5/1991 | Koslow | 264/122 |
| 5,043,090 | 8/1991 | Camp et al. | 252/106 |
| 5,082,655 | 1/1992 | Snipes et al. | 424/486 |
| 5,133,892 | 7/1992 | Chun et al. | 252/90 |
| 5,135,752 | 8/1992 | Snipes | 424/435 |
| 5,139,790 | 8/1992 | Snipes | 424/435 |
| 5,147,722 | 9/1992 | Koslow | 264/122 |

Primary Examiner—Shep K. Rose
Attorney, Agent, or Firm—Vorys, Sater, Seymour & Pease

[57] ABSTRACT

An excipient for a pharmaceutical compound which melts at body temperature but will not spontaneously deform at higher temperatures encountered in shipment and storage comprises:

| | |
|---|---|
| Low MW Polyethylene glycol (M.P. about 37° C.) | 75-90% |
| Medium to high MW polyethylene glycol | 0-4% |
| Long chain saturated carboxylic acid | 0-4% |
| Polyethylene oxide (MW 100,000-5,000,000) | 0-4% |
| Colloidal silica | 10-20%. |

The excipient is particularly advantageous for the preparation of dosage forms for buccal administration of pharmaceutical compounds.

27 Claims, No Drawings

LOW-MELTING MOLDABLE PHARMACEUTICAL EXCIPIENT AND DOSAGE FORMS PREPARED THEREWITH

CROSS-REFERENCE TO RELATED APPLICATION

This is a divisional of copending application(s) Ser. No. 07/677,573, filed on Mar. 29, 1991, U.S. Pat. No. 5,139,790, which is a division of application Ser. No. 07/264,747, filed Oct. 31, 1988, now U.S. Pat. No. 5,004,601, which is a continuation in part of application Ser. No. 07/257,569, filed Oct. 14, 1988, now U.S. Pat. No. 5,135,752.

BACKGROUND OF THE INVENTION

1. Field of the Invention

This invention relates to pharmaceutical excipients and more particularly to moldable excipients suitable for preparing dosage forms. The invention also relates to excipients suitable for preparing dosage forms adapted for transmucosal administration of medicaments.

2. Brief Description of the Prior Art

Pharmaceutical compounds are usually administered in the form of mixtures with other ingredients that provide for convenient measurement of the dose, ease in preparation of the dosage form and desirable physical properties of the dosage form such as shape, size, rate of dissolution, and the like. The non-pharmaceutical ingredients of the composition, known as excipients, often constitute the major portion of the composition of which a particular dosage form is composed. In the preparation of a particular dosage form the active pharmaceutical agent is mixed with the excipients in a proportion calculated to provide a desired unit dose in a convenient size and shape. For example, a medicament may be incorporated into a tabletting mixture in a proportion so that a tablet of convenient size made by compressing the mixture will contain one dose of the drug. Similarly, in the case of an ointment for topical application, the proportion of active ingredient mixed with the ointment base will be chosen so that application of a convenient amount of the ointment to the site to be treated will deliver an effective amount of the medication to the site. In addition to providing a means for measuring the dose of medication, the excipient also provides a matrix for containing and releasing the medication to the site to be treated. Thus, an enteric capsule may provide for gradual release of the medication over a period of time in the gastrointestinal tract, or a transdermal matrix may provide for a continuous supply of medication to the skin surface by diffusion through the matrix.

Thus, the proper adaptation of the excipient to the mode and site of delivery of a drug is important in achieving a desired level of the drug in the bloodstream or in securing effective administration of the medication to the desired tissue.

A particular mode of drug delivery wherein the choice of excipient is important is transmucosal administration, particularly in administration via the mucosa of the oral cavity.

Administration of pharmaceutical compounds through the oral mucosa has been found to be an effective means of supplying an effective dose directly to the bloodstream of a patient. The transmucosal route of administration avoids the possibility that the pharmaceutical compound will be destroyed in the gastrointestinal tract before it can be absorbed, and also eliminates the danger of first-pass inactivation in the liver after absorption. Dosage forms relying on transmucosal absorption in the oral cavity have generally been of the buccal or sublingual type. Typically, the buccal dosage form is placed in the buccal cavity between the gum and the cheek, where it dissolves in the patient's saliva, releasing the medicament into the buccal cavity in close proximity to the capillary bed of the oral mucosa. The pharmaceutically active compound then enters the blood in the capillary bed by diffusion through the mucosal tissue and is distributed in the bloodstream to the rest of the body. The rate at which the medication is supplied to the body depends upon, among other things, the rate at which the buccal dosage form dissolves in the mouth. In particular, with patients who have a deficient flow of saliva, a condition found with some frequency in elderly patients and in patients who may be taking medication which tends to depress the flow of saliva, the dosage form may dissolve slowly and supply the medication at a rate which is slower than desired. Such patients also have to endure the discomfort of retaining a foreign object in the buccal cavity, often between the cheek and gum, for a longer period than they might wish.

In sublingual administration, the dosage form is placed beneath the tongue where it dissolves in the saliva to release the drug for transmucosal absorption. A deficiency of this mode of administration is that, in many cases, a significant fraction of the drug released from the dosage form does not remain in contact with the sublingual mucosa long enough to be absorbed, but is washed into the gastrointestinal tract by the continuous flow of saliva. Thus, sublingual medication partakes of the characteristics of both the transmucosal and gastrointestinal routes of administration.

Other methods of administration of medicaments also rely on transmucosal delivery. For example, rectal suppositories and vaginal suppositories or pessaries can be used to deliver drugs to the bloodstream by transmucosal absorption. The physical properties of the dosage form determine the degree of contact with the mucosal tissues and consequently the efficiency of the absorption of the medicament.

Another mode of administration wherein the dosage form is of consequence is in topical administration of medicaments in an ointment. Antimicrobials, antibiotics, antiinflammatory drugs and drugs affecting the skin, such as those used in treating acne, may be administered in this way. Determining the correct dose has been difficult for drugs administered in an ointment, for the material is usually supplied in a tube or jar containing enough for many applications, and the patient must judge how much to apply. In certain applications wherein dosage is critical, this can lead to application of too little medication, with consequent ineffectiveness, or too much, with consequent systemic effects from unwanted transdermal or transmucosal absorption. In some sites, such as the eye or the vagina, uniform application of an ointment is difficult.

Hence, a need has continued to exist for a pharmaceutical excipient that can provide intimate contact with the site to be treated, to assure maximum transmucosal absorption when that is desired, while being capable of being molded into unit dosage forms which retain their shape under conditions of temperature and handling experienced in marketing. In particular, there is a need for a buccal dosage form which will rapidly disintegrate or lose its perceptible shape in the mouth and thereby rapidly and comfortably release its medicament into the buccal cavity independently of the rate of flow of the patient's saliva.

SUMMARY OF THE INVENTION

This need has now been supplied by the pharmaceutical excipient of this invention which is a water-soluble matrix composition for containing a pharmaceutically active ingredient and which softens essentially to an easily flowable material at body temperature, yet can be molded into unit dosage forms which maintain their shape under the temperature extremes and handling which occur in the normal course of commercial distribution and sale of the medications. The transmucosal embodiments of this invention provide a rapidly disintegrating dosage form for transmucosal administration of medicaments. The pharmaceutical excipient of the invention is a low-melting moldable composition having the following composition, wherein all percentages are by weight:

| Low MW Polyethylene glycol (M.P. about 37° C.) | 75–90% |
| --- | --- |
| Medium to high MW polyethylene glycol | 0–4% |
| Long chain saturated carboxylic acid | 0–4% |
| Polyethylene oxide (MW 100,000–5,000,000) | 0–4% |
| Colloidal silica | 10–20% |

Accordingly, it is an object of the invention to provide a pharmaceutical excipient.

A further object of the invention is to provide a matrix for a transmucosal dosage form.

A further object is to provide a matrix for a buccal dosage form.

A further object of the invention is to provide a rapidly dispersing buccal dosage form.

A further object is to provide a buccal dosage form which disperses rapidly in the buccal cavity at body temperature.

A further object is to provide a buccal dosage form which disperses rapidly in the buccal cavity at body temperature, but retains its shape at elevated temperatures in storage.

A further object is to provide an ointment base for a topical dosage form.

Further objects of the invention will become apparent from the description of the invention which follows.

DETAILED DESCRIPTION OF THE INVENTION AND PREFERRED EMBODIMENTS

It has been found desirable in transmucosal dosage forms which are intended to provide rapid administration of a medicament that the dosage form disperse rapidly in contact with the mucosal tissue and spread over the tissue in intimate contact therewith to provide for rapid and efficient absorption of the medicament. In the case of a buccal dosage form it is desirable to provide a dosage form which disperses rapidly in the buccal cavity to provide a fluid which can cover a relatively large area of the oral mucosa. Conventional buccal dosage forms are dispersed by dissolution in the saliva. The dissolution process takes some time, and some individuals, especially elderly patients, may not produce enough saliva to dissolve the dosage form rapidly enough. The dissolution proceeds from the surface of the dosage form while the dosage form retains its general initial shape. The continued presence in the buccal cavity of the undissolved portion of the dosage form may also be annoying to some patients.

The buccal dosage form using the excipient of this invention has been formulated to provide a dosage form which rapidly disperses in the mouth by reason of softening or melting at body temperature to provide a soft gel which can disperse over a large area of the oral mucosa. The ingredients of the dosage form are also, for the most part, water soluble, so that to the extent possible, the matrix of the dosage form will dissolve in the saliva. Because the dosage form melts or greatly softens when placed in the mouth, the surface area of the matrix available to contact the oral mucosa is also increased, and this assists the absorption of the pharmaceutical ingredient of the dosage form through the oral mucosa. Furthermore, the almost immediate melting of the dosage form avoids the discomfort experienced by some patients because of the continued presence of a perceived foreign body in the buccal cavity.

Similar considerations apply to dosage forms of the invention intended for use in sublingual administration of drugs. Rapid dispersion of the dosage form and intimate contact with the mucosa are desirable to minimize the amount of pharmaceutical compound which is carried down the esophagus by the flow of saliva and not available for transmucosal administration. In rectal and vaginal administration of drugs, it is also desirable to have a dosage form which disintegrates rapidly and permits contact of the drug with the mucosa over a relatively large area to promote rapid absorption.

In topical administration of medicaments such as antimicrobials, it is desirable that the ointment base be soft and easily spread. Furthermore in the case of ointments which are to be applied in locations such as the eye or vagina where it is difficult to assure uniform spreading by manipulation, it is desirable that the ointment effectively melt at body temperature and spread over the tissues to be treated.

A principal ingredient of the dosage form of the invention is a polyethylene glycol (PEG) having a melting point near 37° C., i.e., near body temperature. Polyethylene glycols having molecular weights (MW) in the neighborhood of 1000 are found to have melting points near 37° C. The exact melting point can be adjusted by minor admixtures of PEG's having other molecular weights, as discussed more fully below. When the dosage form comprised largely of the PEG matrix is placed in contact with the site of administration, e.g., the mouth, skin, eye, vagina or rectum, it is rapidly warmed to its melting point whereupon it melts and disintegrates, spreading the medication over the adjacent tissues. In the case of a buccal dosage form, the dosage form rapidly melts and disintegrates within the buccal cavity, thereby carrying the medication into contact with the oral mucosa over a relatively large area. Typically 75–90% by weight of the dosage form is a PEG having a molecular weight of about 1000. Preferably, the amount of PEG 1000 is about 82.5%.

However, a dosage form which melts at the relatively low temperature of 37° C. is in danger of melting or softening and being unacceptably deformed during shipping and storage where it may be exposed to temperatures higher than 37° C. This problem is overcome in the dosage form of this invention by incorporating an amount of colloidal silica effective to stabilize the composition so that the dosage form retains its shape when it is exposed to temperatures above 37° C. The colloidal silica forms a dimensionally stable gel when dispersed in the molten PEG. The gel is transparent above the melting point of the ingredients, but retains its shape sufficiently to withstand deformation by the usual handling when individually packaged in a suitable container. When the gel is cooled to a temperature below the melting point of the ingredients, it again becomes hard and generally opaque. To accomplish this purpose, the amount of colloidal silica ingredient is from about 10% to about 20% by weight, preferably from about 12% to about 18% by weight and most preferably about 16% by weight of the composition.

The composition of the invention containing only a low molecular weight PEG and colloidal silica is stable enough for handling in use and is particularly well adapted to dosage forms, such as suppositories, which are manufactured by casting in molds and then distributed and sold, only being removed from the mold just prior to use. However, for those dosage forms which are packaged in a form wherein they are free to move and contact the wall of the package or other dosage forms within the package, it is preferred to increase the hardness of the excipient by adding a small amount of polyethylene oxide (PEO) having a molecular weight in the range from about 100,000 to about 5,000,000 daltons. The high molecular weight polyethylene oxide contributes strength to the molded dosage form and reduces brittleness. It also improves the ability of the dosage form to be prepared by injection molding. It is preferred to incorporate an amount of PEO ingredient from about 0.1% to about 4% by weight. Preferably PEO having a molecular weight of about 5,000,000 is present in a proportion of about 0.5% by weight.

Other ingredients are added to the composition of the invention to provide particular properties.

A small proportion of a higher molecular weight PEG may be included to provide precise control over the melting point of the lower molecular weight PEG. PEG's having a molecular weight in the range of 3350–8000 are suitable for this purpose. Higher molecular weight PEG's would also be suitable, provided they have the necessary approval of the Food and Drug Administration for use in pharmaceuticals. PEG 8000 is a preferred high molecular weight PEG. The proportion may vary from 0–4% by weight. Typically, about 0.5% by weight of PEG 8000 is included to adjust the melting point.

In order to reduce the hygroscopicity of the dosage form, a small amount of a long chain carboxylic acid is preferably included. The carboxylic acid may have a carbon chain of 12–18 carbon atoms and is preferably a straight chain saturated aliphatic carboxylic acid. Myristic acid is a preferred long chain carboxylic acid. The proportion of long chain carboxylic acid may vary from 0–4% by weight. The preferred amount of long chain carboxylic acid is about 0.5% by weight.

A preferred composition of the matrix of this invention comprises the following ingredients, wherein the percentages are by weight:

| | |
|---|---|
| Polyethylene glycol (MW 1,000) | 82.5% |
| Polyethylene glycol (MW 8,000) | 0.5% |
| Myristic acid | 0.5% |
| Polyethylene oxide | 0.5% |
| Colloidal silica | 16.0% |

When preparing a suppository using the excipient of the invention, when the suppository is to be molded in a disposable mold and distributed still encased in the mold, it is not necessary to incorporate PEO into the matrix, since the suppository is not free to move within the mold. However, it may be desirable under some circumstances, for example when the medicament incorporated into the suppository might migrate into a plastic mold, to remove the suppository from the mold and package it in, e.g., a foil pouch for distribution. In such instances it is preferable to include the PEO in the excipient to provide additional strength, as discussed above.

The pharmaceutical active ingredient incorporated into the excipient of this invention will vary depending on the purpose and site of administration. For topical application, the active ingredient may be an antibiotic, an antimicrobial, an antifungal, e.g, nystatin, miconazole and the like, an antiinflammatory, such as a corticosteroid, or a keratolytic drug such as retinoic acid.

When the excipient of the invention is used in a transmucosal dosage form it may contain any conventional pharmaceutical compound suitable for administration by transmucosal absorption, in particular by absorption through the buccal mucosa, can be incorporated into the dosage form of the invention. Such medicaments include estradiol, synthetic estrogens and progestins, nicotine, prochlorperazine, vitamin $B_{12}$, ergotamine tartrate, scopolamine, nitroglycerine, buprenorphine, epinephrine, methyltestosterone, triazolam, lidocaine, dronabinol, nabilone, calcitonin, pyroxicam, and the like.

The invention will be further illustrated by the following examples which are intended to illustrate the practice of the invention and are not to be construed as implying any limitation on the scope of the invention which is defined only by the appended claims.

EXAMPLE 1

This example illustrates the preparation of placebo buccal dosage forms of the invention for use in comparative experiments.

Placebo buccal tablets were prepared in the following manner. A total of 330 grams of polyethylene glycol (MW 1000) was melted and maintained at approximately 75° C. To this was added 2 grams of polyethylene glycol (MW 8000) and 2 grams of myristic acid. The mixture was stirred for approximately 5 minutes. Thereupon, 2 grams of polyethylene oxide (MW 5,000,000) was slowly added and mixed for approximately 45 minutes to effect dissolution. Next was added 64 grams of colloidal silica, and the mixture was blended until smooth and homogeneous. The matrix thus prepared was spread in a thin layer and allowed to solidify at room temperature. A portion of the hardened matrix was granulated and fed into an injection molding machine. By this process placebo buccal tablets were prepared having a thin elongated oval shape.

EXAMPLE 2

This example illustrates the preparation of a buccal dosage form of this invention.

Buccal tablets containing methyltestosterone were prepared by a procedure similar to that of Example 1.

Each injection molded buccal tablet had the following composition:

| Ingredient | Amount (mg) |
| --- | --- |
| Polyethylene glycol (MW 1,000) | 31.25 |
| Polyethylene glycol (MW 8,000) | 0.25 |
| Myristic acid | 0.25 |
| Polyethylene oxide | 0.25 |
| Methyltestosterone | 10.0 |
| Colloidal silica | 8.0 |

EXAMPLE 3

This example compares the rate of dissolution of the buccal dosage form of this invention with that of a commercial buccal tablet.

The buccal methyltestosterone tablet of Example 2 was compared with a commercial buccal methyltestosterone product containing the same quantity of drug. The test was designed to examine how fast each buccal tablet disappeared in the buccal cavity. Six male volunteers placed a buccal methyltestosterone tablet of Example 2 in the lower frontal buccal space on one side of the mouth and the prior art commercial buccal methyl testosterone product at a comparable location on the opposite side of the mouth. The tablets were located inside the lower lip but outside the tooth line. At various times thereafter, the lower lip was pulled forward and a monitor inspected buccal space visually for disappearance of the buccal tablet. By this procedure the time to dissolve was evaluated for each buccal tablet in each volunteer. The results are shown in Table 1.

TABLE 1

| | Time to Disappearance (minutes) | |
| --- | --- | --- |
| Subject | Prior Art Commercial Buccal Tablet | Buccal Tablet of Example 2 |
| 1 | >60 | 12 |
| 2 | 45 | 6 |
| 3 | 45 | 3 |
| 4 | 33 | 6 |
| 5 | >60 | 3 |
| 6 | >60 | 9 |
| Mean | >50.5 | 6.5 |

These data show that the buccal methyltestosterone tablet of Example 2 disappears much faster than the prior art commercial buccal methyltestosterone product. Additionally, comparisons between the buccal placebo tablets of Example 1 and prior art buccal placebo tablets under development at another laboratory revealed that the buccal placebo tablet of Example 1 disappeared much faster than the prior art developmental tablet. Collectively, these studies establish that the buccal tablets of the present invention are rapid, in comparison to prior art buccal tablets, in disappearance from the buccal cavity.

EXAMPLE 4

This example illustrates preparation of buccal tablets of the invention containing estradiol as the active ingredient.

Buccal tablets containing estradiol were prepared by a procedure similar to that of Example 1. Each oval-shaped buccal tablet had dimensions of 1.0 millimeters by 5.0 millimeters by 10 millimeters, weighed 54 milligrams, and contained 0.2 milligrams of estradiol. In preparing the matrix, the drug was added just prior to addition of the colloidal silica. The formulation, stated in the order in which components were added, is as follows:

| Ingredient | Percent by weight |
| --- | --- |
| Polyethylene glycol (MW 1000) | 82.13 |
| Polyethylene glycol (MW 8000) | 0.50 |
| Myristic acid | 0.50 |
| Polyethylene oxide (MW 5,000,000) | 0.50 |
| 17-beta-estradiol U.S.P. | 0.37 |
| Colloidal silica | 16.00 |

EXAMPLE 5

This example illustrates the rapid achievement of therapeutic blood levels using the buccal tablets of the invention.

A bioavailability study was carried out using the estradiol buccal tablets of Example 4. Six postmenopausal women volunteers took part in the trial. For each volunteer, an estradiol buccal tablet was placed in the buccal cavity at time zero. At appropriate time intervals thereafter, blood samples were drawn and subsequently analyzed for serum estradiol concentration. Table 2 gives values for the time to reach maximum estradiol levels ($T_{max}$) and the maximum estradiol concentration reached ($C_{max}$) for each of the six subjects.

TABLE 2

| Subject | $T_{max}$ (hours) | $C_{max}$ (picograms/ml) |
| --- | --- | --- |
| 1 | 0.5 | 1180 |
| 2 | 0.75 | 884 |
| 3 | 0.5 | 1248 |
| 4 | 1.0 | 925 |
| 5 | 1.0 | 817 |
| 6 | 0.5 | 829 |
| Mean | 0.71 | 980 |

These results show that estradiol is rapidly and efficiently absorbed into the blood stream by administration of the estradiol buccal tablets of this invention.

EXAMPLE 6

This example illustrates the preparation of buccal tablets containing nicotine as the active ingredient.

Buccal tablets containing nicotine, to be used as an aid in smoking cessation programs, were prepared as follows. A total of 82 grams of polyethylene glycol (MW 1000) was melted and maintained at 75° C. To this was added 0.5 gram of polyethylene glycol (MW 8000), 0.5 gram of myristic acid, 1.0 gram of citric acid, and 0.5 gram of polyethylene oxide (MW 5,000,000). After dissolution was complete the mixture was cooled to 60° C. Next, 1.0 gram of nicotine was blended into 2.0 grams of colloidal silica, and the blend was added slowly to the other ingredients. Finally, an additional quantity of 12.5 grams of colloidal silica was added and mixing was continued until the molten composition was smooth and homogeneous. The matrix was cooled, granulated, and injection molded to form dosage units weighing 50 milligrams and containing 0.5 milligram of nicotine.

EXAMPLE 7

This example illustrates the administration of nicotine using the buccal tablets of this invention.

Six volunteers, including smokers and non-smokers, placed a nicotine buccal tablet of Example 6 in his or her buccal cavity. Each reported that, within 2 to 5 minutes, physiological effects were felt similar to those experienced or known to exist when smoking cigarettes, i.e., light headedness, tachycardia, and tingling sensations in peripheral extremities. These results indicate that nicotine is rapidly absorbed by administration of nicotine buccal tablets of the present invention.

EXAMPLE 8

This example illustrates the preparation of comparative buccal tablets lacking the colloidal silica ingredient.

Placebo buccal tablets lacking colloidal silica were prepared by a procedure similar to that of Example 1. The composition of these tablets was a follows:

| Ingredient | Percent by weight |
|---|---|
| Polyethylene glycol (MW 1000) | 98.5 |
| Polyethylene glycol (MW 8000) | 0.5 |
| Myristic acid | 0.5 |
| Polyethylene oxide (MW 5,000,000) | 0.5 |

EXAMPLE 9

This example illustrates the shape-retaining properties of the buccal tablets of this invention at elevated temperatures.

Injection molded placebo tablets of Example 8 were compared with those of Example 1 in the following manner. Tablets of Example 8 and tablets of Example 1 having identical size and shape were placed on a flat surface and the test assembly was placed in an incubator at 40° C. Within a few minutes the tablets of Example 8, devoid of colloidal silica, had melted, flattened out on the surface, and had lost all resemblance to their original shape. The tablets of Example 1, however, became optically clear at 40° C. but retained their original shape and were not deformed by gravity. Fine structural details, such as ejector pin marks from the injection molding machine, were retained at 40° C., even though the tablets were a soft gel and could be easily mashed. When the tablets of Example 1 were allowed to cool to room temperature, they became hard again and were virtually identical to tablets not exposed to high temperature. These experiments were repeated at higher temperatures and for longer heating times. In one experiment, tablets cf Example 1 kept at 45° C. for 48 hours retained their original shape. These results prove that colloidal silica is an essential ingredient to provide a buccal tablet that has shape retention in the molten state. This property is of considerable value, providing a buccal tablet that can be individually blister packaged and maintain its integrity under adverse thermal exposure during shipping and storage.

EXAMPLE 10

This example illustrates the preparation of buccal tablets which do not contain the optional polyethylene oxide ingredient of the preferred embodiment of the invention.

Placebo buccal tablets non containing polyethylene oxide were prepared by a procedure similar to that of Example 1. The composition of the matrix was as follows:

| Ingredient | Percent by weight |
|---|---|
| Polyethylene glycol (MW 1000) | 83.0 |
| Polyethylene glycol (MW 8000) | 0.5 |
| Myristic acid | 0.5 |
| Colloidal silica | 16.00 |

EXAMPLE 11

This example illustrates the beneficial results of incorporating polyethylene oxide according to the preferred embodiment of the invention.

Injection molded placebo tablets of Example 10 were compared with those of Example 1 for their shape retention properties in the molten state. It was observed that tablets of Example 10 did not retain their shape at 40° C. or 45° C. in the same manner as tablets of Example 1, although the difference was not as great as for those lacking colloidal silica (tablets of Example 8). These results, along with those of Example 9, show that both polyethylene oxide and colloidal silica are essential for optimal shape retention in the molten state.

EXAMPLE 12

This example illustrates the preparation of buccal tablets lacking the myristic acid ingredient of the buccal tablets of this invention.

Placebo buccal tablets lacking myristic acid were prepared by a procedure similar to that of Example 1. The composition of these tablets was as follows:

| Ingredient | Percent by weight |
|---|---|
| Polyethylene glycol (MW 1000) | 83.0 |
| Polyethylene glycol (MW 8000) | 0.5 |
| Polyethylene oxide (MW 5,000,000) | 0.50 |
| Colloidal silica | 16.00 |

EXAMPLE 13

This example illustrates the comparative humidity absorption of dosage forms of the invention compared with those which are devoid of myristic acid.

Injection molded placebo tablets of Example 12 were compared with those of Example 1 in the following manner. Tablets of Example 12 and those of Example 1 were carefully weighed and placed in enclosed chambers of known relative humidity. At appropriate times thereafter the samples were removed briefly and weighed to provide a measure of moisture uptake. These data are given in Table 3 and Table 4 for relative humidities of 42% and 79% respectively.

TABLE 3

| Moisture Uptake at 42% Relative Humidity | | |
|---|---|---|
| | Weight increase (percent) | |
| Time (hours) | Tablets of Example 1 | Tablets of Example 13 |
| 0.5 | 0.43 | 0.59 |
| 1 | 0.76 | 0.88 |
| 2 | 0.88 | 1.51 |
| 3 | 1.17 | 1.53 |
| 4 | 1.38 | 2.07 |
| 24 | 2.14 | 2.48 |

TABLE 4

| | Moisture Uptake at 79% Relative Humidity | |
|---|---|---|
| | Weight increase (percent) | |
| Time (hours) | Tablets of Example 1 | Tablets of Example 13 |
| 0.5 | 0.82 | 1.37 |
| 1 | 1.41 | 2.19 |
| 2 | 2.34 | 3.79 |
| 3 | 3.28 | 4.91 |
| 4 | 4.10 | 6.27 |
| 24 | 17.52 | 19.32 |

These results show that the inclusion of myristic acid in the buccal tablet formulation of this invention results in a less hygroscopic product. This property is of value in the manufacturing and packaging of buccal tablets of the present invention.

EXAMPLE 14

This example illustrates the preparation of buccal tablets with and without the inclusion of polyethylene glycol of molecular weight 8,000.

Placebo buccal matrices lacking polyethylene glycol (MW 8,000) and containing 2% polyethylene glycol (MW 8,000) were prepared by a procedure similar to that used in preparing the matrix of Example 1 The compositions of these two matrices are as follows:

| | Percent (by weight) | |
|---|---|---|
| Ingredient | Matrix A | Matrix B |
| Polyethylene glycol (MW 1000) | 83 | 81 |
| Polyethylene glycol (MW 8000) | 0 | 2 |
| Myristic acid | 0.5 | 0.5 |
| Polyethylene oxide (MW 5,000,000) | 0.5 | 0.5 |
| Colloidal silica | 16 | 16 |

EXAMPLE 15

This example illustrates the comparative melting points of the compositions prepared in Example 14.

The melting points were determined for the matrices of Example 14 and the matrix of Example 1. The results are shown in Table 5.

TABLE 5

| Matrix | PEG (MW 8,000) (percent) | Melting range (°C.) |
|---|---|---|
| Example 14A | 0 | 35.5-36.0 |
| Example 1 | 0.5 | 36.0-36.5 |
| Example 14B | 2.0 | 38.5-39.0 |

These results show that small quantities of polyethylene glycol (MW 8,000) can be used to regulate the melting point of the buccal matrix in the range of body temperature.

EXAMPLE 16

This example illustrates the preparation of a suppository using the excipient of the invention.

A composition was prepared by the general procedure of Example 1 having the following composition:

| Ingredient | Percent by weight |
|---|---|
| Polyethylene glycol (MW 1000) | 84.9957 |
| Myristic acid | 1.00 |
| Salmon calcitonin | 0.0043 |
| Water | 0.25 |
| Colloidal silica | 13.75 |

The salmon calcitonin was added as an aqueous solution to the molten mixture of PEG and myristic acid.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims ar intended to be embraced therein.

I claim:

1. A composition for a buccal dosage form comprising a pharmaceutical compound suitable for administration by diffusion through the buccal mucosa dispersed in a matrix consisting essentially of:

| Ingredient | Percent by weight |
|---|---|
| Low MW Polyethylene glycol (M.P. about 37° C.) | 75-90% |
| Medium to high MW polyethylene glycol | 0-4% |
| Polyethylene oxide (MW 100,000-5,000,000) | 0.1-4% |
| Colloidal silica | 10-20%. |

2. The composition of claim 1 wherein said low MW polyethylene glycol is PEG 1000.

3. The composition of claim 1 wherein said medium to high MW polyethylene glycol is PEG 8000.

4. The composition of claim 1 wherein said polyethylene oxide has a MW of about 5,000,000.

5. The composition of claim 1 wherein said medium to high molecular weight PEG is present in a proportion of about 0.5% by weight.

6. The composition of claim 5 wherein said medium to high molecular weight PEG is PEG 8000.

7. The composition of claim 1 wherein said polyethylene oxide is present in a proportion of about 0.5% by weight.

8. The composition of claim 7 wherein said polyethylene oxide has a molecular weight of about 5,000,000.

9. The composition of claim 8 wherein said colloidal silica is present in a proportion of about 12% to about 18% by weight.

10. The composition of claim 9 wherein said colloidal silica is present in a proportion of about 16% by weight.

11. A dosage form comprising a pharmaceutical compound dispersed in a matrix consisting essentially of

| Ingredient | Percent by weight |
|---|---|
| Low MW Polyethylene glycol (M.P. about 37° C.) | 75-90% |
| Medium to high MW polyethylene glycol | 0-4% |
| Polyethylene oxide (MW 100,000-5,000,000) | 0.1-4% |
| Colloidal silica | 10-20%. |

12. The dosage form of claim 11 wherein said low MW polyethylene glycol is PEG 1000.

13. The dosage form of claim 11 wherein said medium to high MW polyethylene glycol is PEG 8000.

14. The dosage form of claim 11 wherein said polyethylene oxide has a MW of about 5,000,000.

15. The dosage form of claim 11 wherein said low molecular weight polyethylene glycol is PEG 1000.

16. The dosage form of claim 11 wherein said medium to high molecular weight PEG is present in a proportion of about 0.5% by weight.

17. The dosage form of claim 11 wherein said medium to high molecular weight PEG is PEG 8000.

18. The dosage form of claim 11 wherein said polyethylene oxide is present in a proportion of about 0.5% by weight.

19. The dosage form of claim 18 wherein said polyethylene oxide has a molecular weight of about 5,000,000.

20. The dosage form of claim 11 wherein said colloidal silica is present in a proportion of about 12% to about 18% by weight.

21. The dosage form of claim 20 wherein said colloidal silica is present in a proportion of about 16% by weight.

22. The dosage form of claim 11 wherein said dosage form is a buccal dosage form.

23. The dosage form of claim 11 wherein said dosage form is a sublingual dosage form.

24. The dosage form of claim 11 wherein said dosage form is a suppository.

25. The dosage form of claim 11 wherein said dosage form is a pessary.

26. The composition of claim 1 wherein said pharmaceutical compound is selected from the group consisting of nicotine, estradiol, synthetic estrogens and synthetic progestins, prochlorperazine, Vitamin $B_{12}$, ergotamine tartrate, scopolamine, nitroglycerin, buprenorphine, epinephrine, methyltestosterone, triazolam, dronabinol, nabilone, and piroxicam.

27. The dosage form of claim 11 wherein said pharmaceutical compound is selected from the group consisting of nicotine, estradiol, synthetic estrogens and synthetic progestins, prochlorperazine, Vitamin $B_{12}$, ergotamine tartrate, scopolamine, nitroglycerin, buprenorphine, epinephrine, methyltestosterone, triazolam, dronabinol, nabilone, and piroxicam.

* * * * *